United States Patent [19]

Irvin et al.

[11] Patent Number: 4,954,046
[45] Date of Patent: Sep. 4, 1990

[54] PERISTALTIC PUMP WITH MECHANISM FOR MAINTAINING LINEAR FLOW

[75] Inventors: Ronald D. Irvin, Ramona, Calif.; David Burkett, Baldwin, Ga.; David E. Kaplan, Moraga; Ronald J. Harvey, Escondido, both of Calif.

[73] Assignee: IMED Corporation, San Diego, Calif.

[21] Appl. No.: 447,880

[22] Filed: Dec. 8, 1989

[51] Int. Cl.⁵ .............................................. F04B 43/12
[52] U.S. Cl. ...................................... 417/53; 417/474; 128/DIG. 12; 604/153
[58] Field of Search .................... 417/53, 63, 474, 475; 604/151, 153; 128/DIG. 12

[56] References Cited

U.S. PATENT DOCUMENTS

| | | | |
|---|---|---|---|
| 2,393,838 | 1/1946 | Tarbox | 417/474 |
| 3,658,445 | 4/1972 | Pulman et al. | 417/474 |
| 3,778,195 | 12/1973 | Bamberg | 417/479 X |
| 4,191,184 | 3/1980 | Carlisle | 128/DIG. 12 X |
| 4,493,706 | 1/1985 | Bolsanyi et al. | 417/474 X |
| 4,653,987 | 3/1987 | Tsuji et al. | 128/DIG. 12 X |
| 4,671,792 | 6/1987 | Borsanyi | 128/DIG. 12 X |
| 4,728,265 | 3/1988 | Cannon | 417/474 X |

Primary Examiner—Leonard E. Smith
Assistant Examiner—Eugene L. Szczecina, Jr.
Attorney, Agent, or Firm—Nydegger & Harshman

[57] ABSTRACT

A linear peristaltic pump includes a mechanism for maintaining linear flow of fluid through an I.V. tube. The mechanism comprises a casing carrying a rotatable camshaft having a plurality of cams spaced therealong in helical arrangement and a plurality of fingers coupled to the camshaft. A housing for establishing linear reciprocal movement of the fingers in response to rotation of the shaft establishes a moving zone of occlusion along a tube held against the fingers. Aligning means are included for establishing an axis of rotation of the camshaft which is slightly tilted with respect to the tube. This is accomplished by raising or lowering the upstream or the downstream end of the camshaft to prevent unwanted pressure from building up in the tube to reduce pulsatile flow and maintain linear flow. The aligning mechanism comprises a generally cylindrical bushing having an eccentric hole therethrough for carrying the hinged connection between the casing and the housing. The bushing has a slot therethrough for adjustably rotating the bushing for adjusting the amount of tilt. The adjustment can take place during operation of the pump, having a pressure sensor against the tube, to achieve the optimal positioning of the camshaft depending on the tolerances of the pump mechanism to establish linear flow of fluid through the tube.

17 Claims, 3 Drawing Sheets

PERISTALTIC PUMP WITH MECHANISM FOR MAINTAINING LINEAR FLOW

BACKGROUND OF THE INVENTION

The present invention relates generally to peristaltic pumps which are used to pump fluids through resilient tubes. More specifically, the present invention relates to the drive mechanism of a linear peristaltic pump for reducing pulsatile flow and maintaining linear flow of fluids through the tube. The present invention is particularly, but not exclusively, useful in the health care field for intravenous administration of medical solutions to patients.

DISCUSSION OF THE PRIOR ART

Various devices have been proposed which are specifically and uniquely designed for intravenous (I.V.) infusion of medical solutions to patients. The objective in each instance is to provide a device which can reliably and accurately control the flow of fluid to the patient.

Although the actual design for a linear peristaltic pump may differ from pump to pump, all such pumps basically require the mechanical interaction of a resilient tube through which the fluid is to pumped, a platen for providing a hard surface against which the tube can be held, a peristaltic apparatus capable of creating a moving zone of occlusion along the tube, and a drive mechanism for the peristaltic apparatus. For its operation, the linear peristaltic pump must cause these elements to cooperate in a precise manner. Specifically, the peristaltic apparatus must operatively engage the I.V. tube through which the medical solutions are to be pumped, which requires placement of the tub between the platen and the peristaltic apparatus.

With respect to generating a moving zone of occlusion by the linear peristaltic pump, the tube is sequentially occluded by a series of occlusion members, such as fingers which press the tube against the platen. The series of fingers are sequentially pressed against the resilient tube to provide a wavelike occlusion action for smoothly urging fluid through the tube. Generating such occluding action requires finely tuned cooperation between the components of the pump. Unless the components of the device have been properly engineered within precise tolerances, uneven forces may develop and the occluding action can even result in a seizure or stoppage of the device. Obviously such an occurence should be avoided.

In addition to the problem of seizure or stoppage of the pump, uneven forces generated by the pump operation can also create problems with the rate of flow of fluid through the tube. Specifically, even though the pump may continue to operate, any excessive occlusion or pinching forces on the tube can cause deformations of the tube resulting in uncontrolled variations in fluid flow through the tube. This results in a pulsatile fluid flow through the tube, rather than linear flow as desired. Also, excessive occlusion forces can cause fragments to break off the tube with the danger of infusion of such fragments to the patient.

As implied above, mechanical problems with peristaltic pumps often stem from difficulties in achieving the precise engineering tolerances required between its interactive parts for proper operation. These problems are particularly pronounced since tolerances tend to back up into the movement of the pump. Thus, each pump will react and behave differently to the same problem.

One manner in which excessive forces in these peristaltic pumps can be alleviated is to utilize a hinged attachment between the peristaltic drive mechanism and its associated platen. An example of such an I.V. pump is disclosed in U.S. Pat. No. 4,728,265 to Cannon, which is assigned to Fisher Scientific Group Inc. doing business as IMED Corporation, a subsidiary of the assignee of the present invention. The I.V. pump disclosed in U.S. Pat. No. 4,728,265 includes a biasing element which urges the peristaltic mechanism toward the platen, but which yields, as necessary, to limit the force the peristaltic mechanism can exert against the tube. While this provides a solution to the problems caused by excessive forces which may cause a seizure or stoppage of the device, such a structure in and of itself does not readily provide a solution to the problem of pulsatile fluid flow.

The pulsatile fluid flow problem associated with linear peristaltic pumps is caused primarily by the fact that each finger of the pumping mechanism has a discrete effect on the fluid in the tube. The discrete nature of this effect can be reduced by increasing the number of fingers which are making sequential contact with the tube. Unfortunately, even with an optimal number of fingers, there remains a problem in that to establish a continuous wave cycle, it is necessary that the first finger begin a new occlusion cycle at precisely the same time the last finger is terminating the previous cycle of occlusion. Unfortunately, it invariably happens that the first finger and the last finger occlude the tube at the same time, trapping fluid therebetween within a pocket in the tube. The pressing engagement of other fingers between the first and last fingers which sequentially urge against the tube while the pocket is formed between the two points of occlusion causes an increase in pressure with respect to the downstream fluid. As the downstream finger is then lifted off the tube, fluid surges from the pocket and through the line in a nonlinear or pulsatile flow of fluid to the patient.

Ideally, the most downstream finger (last finger) of a linear peristaltic pump will be lifting off (i.e. unoccluding the tube) at precisely the same instant in time that the most upstream finger (first finger) is occluding the tube. With this cooperation of structure, there would be no pocket formed on the tube within which fluid pressure could build up. Unfortunately, ordinary manufacturing practices, machine tolerances, and typical assembly procedures each separately introduce variances during the assembly of a linear peristaltic pump which cause each pump to have individually distinctive pumping characteristics. Consequently, without some means for post-assembly adjustment, each linear peristaltic pump will, to a greater or lesser degree, produce a pulsatile flow of fluid to a patient.

The present invention recognizes that a proper alignment of the linear peristaltic mechanism with its platen will minimize surging in the flow of fluid which can cause difficulties during the injection of medicinal fluids into a patient. Further, the present invention recognizes that a proper alignment can be attained with a post-assembly adjustment.

In light of the above, the present invention addresses the problems associated with linear peristaltic pumps having to do with maintaining a linear flow of fluid to the patient.

Accordingly, it is an object of the present invention to provide a peristaltic pumping apparatus which reduces the pulsatile nature of fluid flow through a tube resulting from the peristaltic action. Another object of the present invention is to provide a linear peristaltic pump which is easy to manufacture and which can be adjusted to compensate for variances from the extremely close tolerances between its mechanical components which are necessary for proper assembly and operation. Yet another object of the present invention is to provide a durable and reliable peristaltic pump which is cost effective and which accurately infuses fluids to patients.

SUMMARY OF THE INVENTION

A preferred embodiment of the linear peristaltic pump of the present invention includes a mechanism for providing a substantially linear flow of fluid through an I.V. tube. More specifically, the preferred embodiment comprises a casing on which a rotatable shaft is operatively mounted which has a plurality of cams mounted upon it that are spaced in a helical arrangement. A plurality of fingers are operatively associated with and driven by the cams mounted on the cam shaft. A housing is hingedly attached to the casing via hinge pins to receive and guide the fingers for establishing linear reciprocal movement of the fingers through the housing in response to rotation of the shaft. A platen portion, with a tube resting thereon is positioned on the housing under the fingers. Activation of the fingers by the rotating cam shaft causes the fingers to engage the tube to establish a moving zone of occlusion along the tube. A spring is connected between the casing and housing to resiliently bias the fingers in the casing against the I.V. tube resting on the platen portion of the housing. An aligning means which interacts between the casing and the housing is provided to properly orient the camshaft. This orientation establishes an axis of rotation for the camshaft which properly aligns the camshaft with respect to the tube resting on the platen to cause the last finger (i.e. downstream finger) to unocclude the tube at the same instant the first finger (i.e. upsteam finger) occludes the tube. With proper adjustment, the time during which the first and last fingers simultaneously occlude the tube is minimized. Thus, any pocket formed between these fingers will exist only momentarily and, consequently, any unwanted pressure build up will be minimal. In one embodiment of the invention, the aligning means is a bushing eccentrically mounted on an upstream hinge pin. The bushing is mounted on the housing so it may be rotated to a desired position to adjust the angle of tilt of the axis of rotation of the camshaft relative to the plane of the platen for controlling its effect on the flow of fluid.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINTGS

Figure 2:
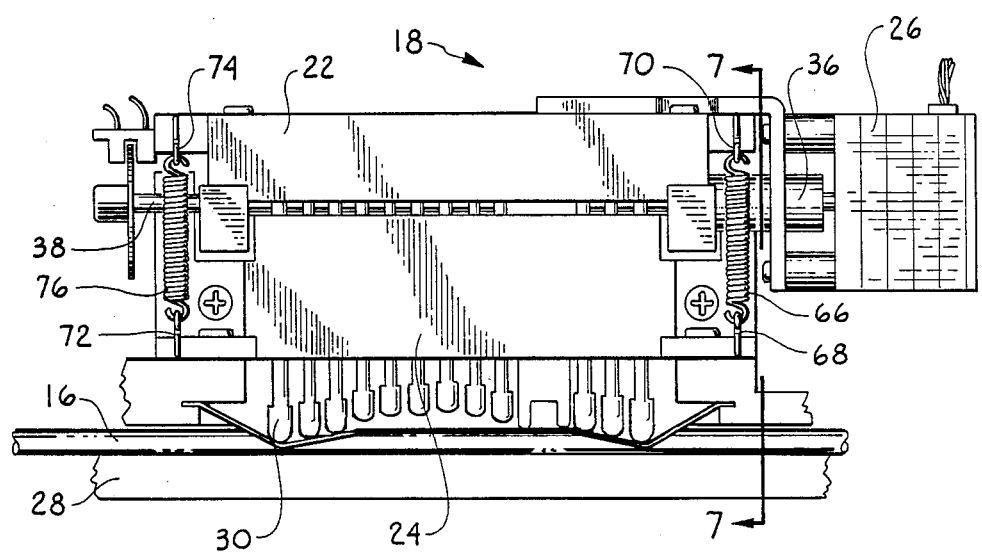
FIG. 2 is a side elevational view of the pumping mechanism of the present invention.
Figure 3:
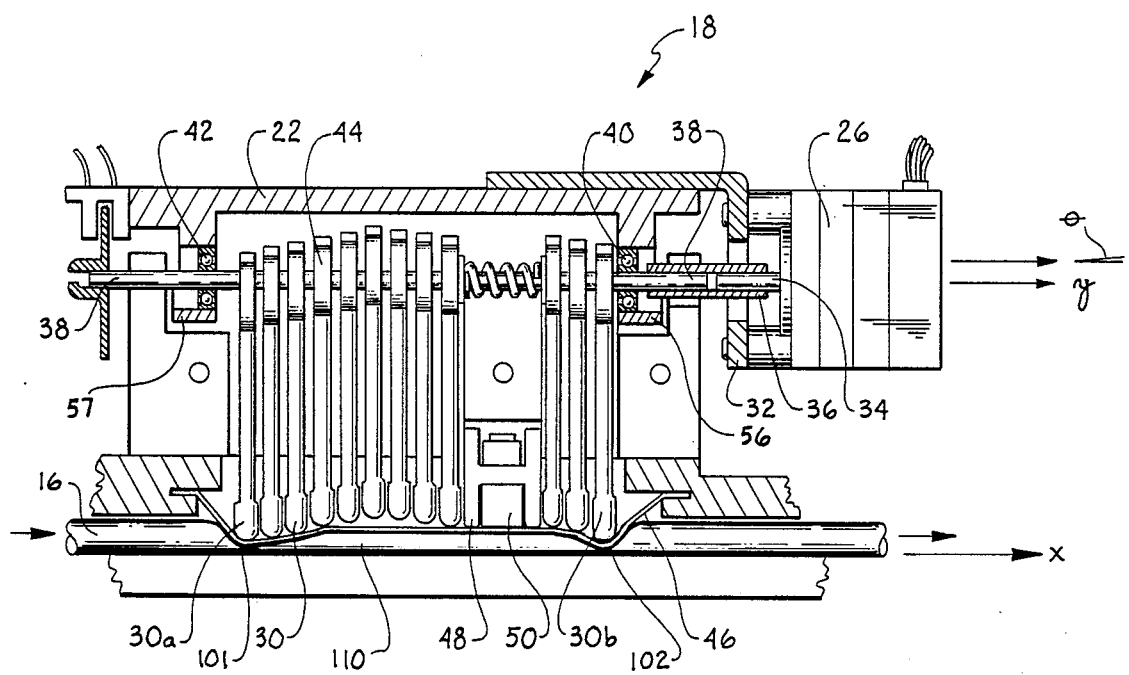
FIG. 3 is a side cross-sectional view taken parallel to the center line of the pumping mechanism of the present invention which corresponds to the view seen in FIG. 2.
Figure 4:
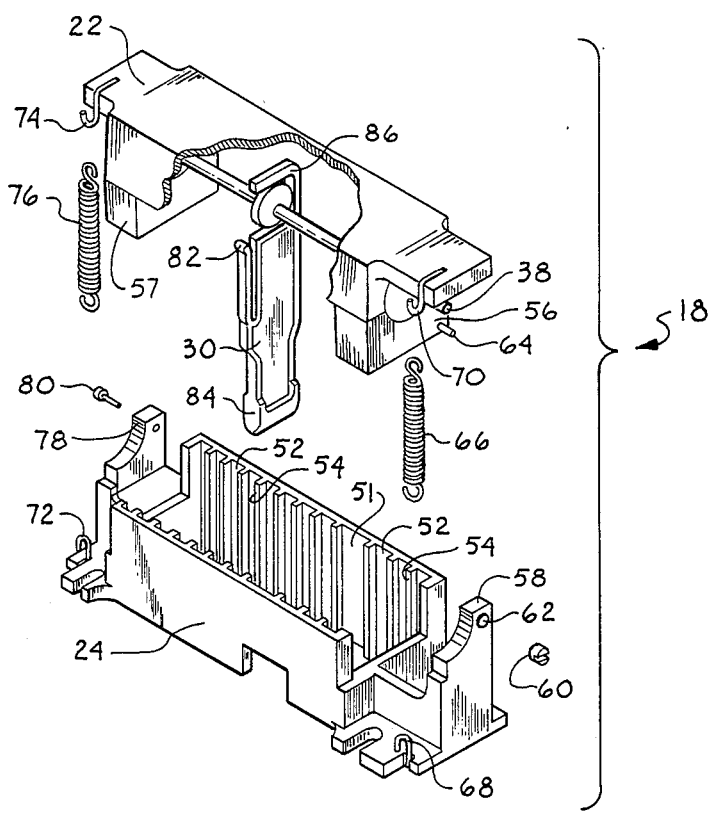
FIG. 4 is an exploded perspective view of the pumping mechanism with portions cut away for clarity.
Figure 6A:
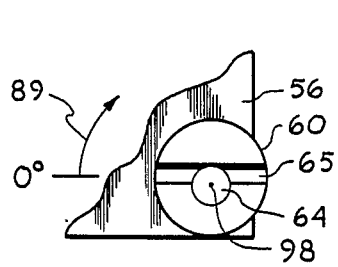
FIG. 6A is an end view of an alignment bushing in a first position of angular rotation.
Figure 6B:
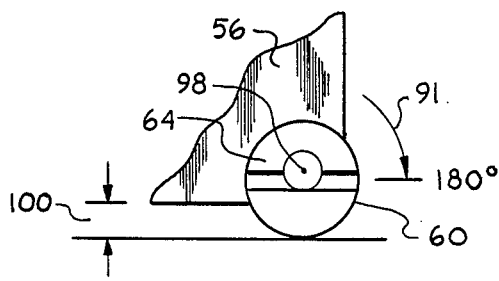
FIG. 6B shows the alignment bushing of FIG. 6A in a rotational position 180° from that of FIG. 6A.
Figure 7A:
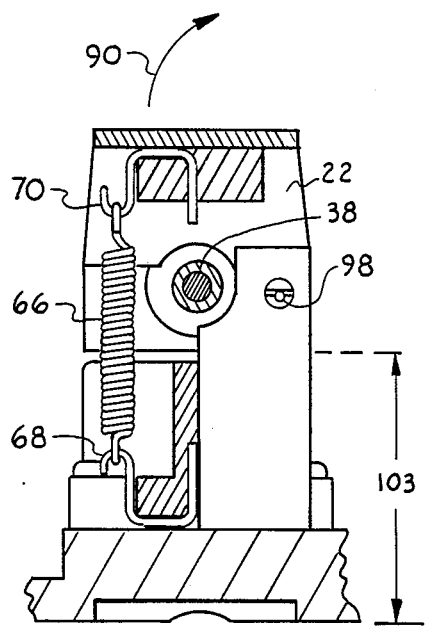
Figure 7B:
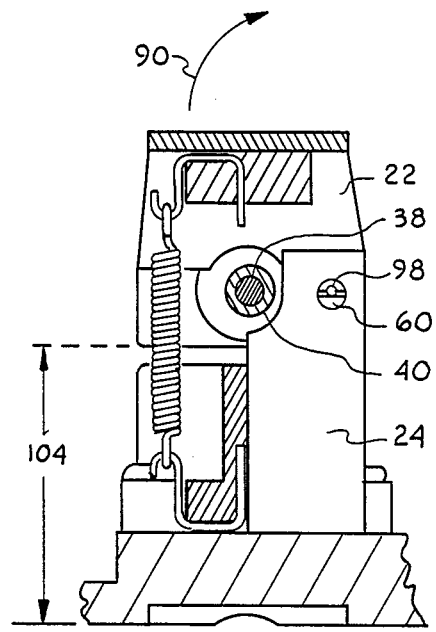

FIG. 7A is a cross-sectional view of the pumping mechanism as seen along the line 7—7 in FIGS. 2 and 4 with the aligning mechanism in position as shown in FIG. 6A; and FIG. 7B is a cross-sectional view of the pumping mechanism as seen along line 7—7 in FIGS. 3 and 4, with the aligning mechanism in position as shown in FIG. 6B.

DESCRIPTION OF THE PREFERRED EMBODIMENT

Figure 1:
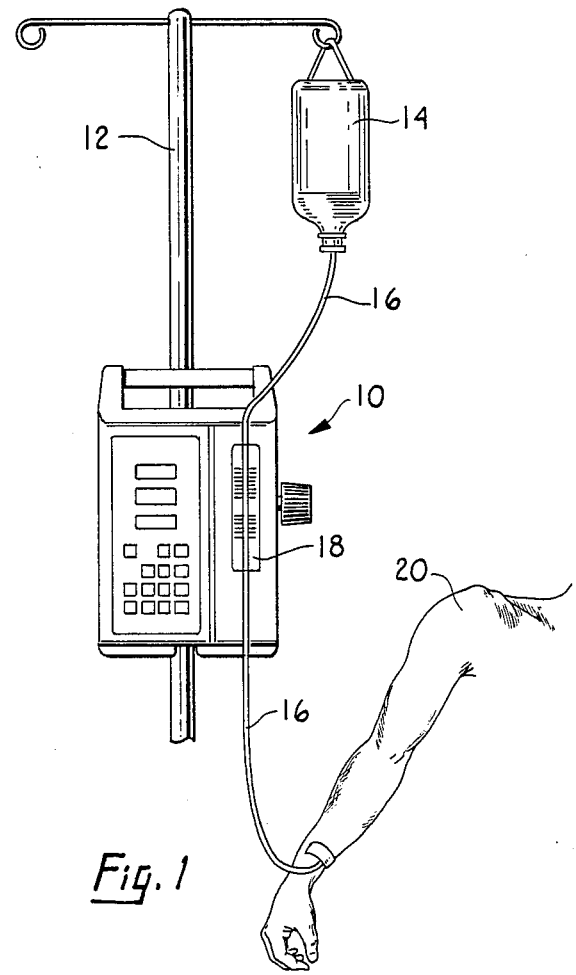
FIG. 1 is a front elevational view of a linear peristaltic pump incorporating the present invention shown in is working environment.

Referring initially to FIG. 1, the present invention is shown in use in its intended environment. In FIG. 1, a linear peristaltic pump generally designated 10 is shown mounted on an I.V. pole 12. A fluid source 14 is suspended from I.V. pole 12 in a conventional manner, and I.V. tube 16 is connected in fluid communication with fluid source 14 for operatively engaging the pumping mechanism 18 of linear peristaltic pump 10. FIG. 1 further shows that I.V. tube 16 extends downstream from linear peristaltic pump 10 and is attached to patient 20.

Referring now to FIG. 2, the general arrangement of the major components of the pumping mechanism 18 is illustrated. Specifically, pumping mechanism 18 includes a casing 22, a housing 24, and a drive motor 26, all of which are operatively associated with a platen 28. Drive motor 26 is operatively associated with casing 22 for moving peristaltic fingers 30 against I.V. tube 16 which is supported and held against platen 28. As is well known in the pertinent art, the action of peristaltic fingers 30 against I.V. tube 16 which is positioned between peristaltic fingers 30 and the platen 28, creates a moving zone of occlusion in wavelike fashion along tube 16 for pumping fluid through tube 16 to patient 20.

In FIG. 3, it is further shown that drive motor 26 is attached to bracket 32. Any conventional means of attachment, such as screws, can be used to establish a fixed positional relationship between the drive motor 26 and bracket 32. Drive motor 26 has a drive shaft 34. A sleeve 36 connects drive shaft 34 with camshaft 38 so that rotational motion of drive shaft 34 is transferred through sleeve 36 to camshaft 38. Casing 22 includes a bearing 40 supported by bearing cap 56, and a bearing 42 supported by bearing cap 57, which support camshaft 38 for rotation relative to casing 22. Bracket 32 is fixedly attached to casing 22 in a manner that holds drive motor 26, camshaft 38 and casing 22 in the relationship shown in FIG. 3. Specifically, these components hold camshaft 38 substantially parallel to the surface of platen 28, subject to further adjustable alignment as further described below.

As further shown in FIG. 3, arranged along the length of camshaft 38 are a series of cams 44. Cams 44 are arranged lengthwise along camshaft 38 in a helical fashion. This arrangement of cams along camshaft 38, when operatively coupled with peristaltic fingers 30, causes a sequential reciprocal motion of the peristaltic fingers 30 that results in a peristaltic action of the fingers 30 against I.V. tube 16. This wavelike action causes a moving zone of occlusion for moving fluid through the tube 16.

There is also shown in FIG. 3 a membrane 46 which separates the peristaltic fingers 30 from I.V. tube 16. The membrane 46 serves as a barrier to prevent unwanted entry of fluids into the working components of the pumping mechanism 18. Pumping mechanism 18 may also incorporate stationary members 48 and a pressure sensor 50.

The cooperation of structure between casing 22 and housing 24 is illustrated further with reference to FIG. 4. The open bottom of housing 24 provides for the extension of peristaltic fingers 30 therethrough, and for the consequent operative engagement of peristaltic fingers 30 with I.V. tube 16. The interior side walls 51 of housing 24 are formed with a series of grooves 52, arranged in side-by-side relationship and separated by guides 54. The grooves 52 receive the peristaltic fingers 30 therein and guides 54 are intended to maintain peristaltic fingers 30 within grooves 54 for linear reciprocal action therein.

The attachment of casing 22 to housing 24 is accomplished by a hinged relationship. To accomplish this connection, bearing cap 56 mounted on casing 22 has a downstream hinge pin 64. Hinge pin 64 is inserted into a hinge alignment bushing 60 which is inserted into hole 62 to establish the hinged relationship between casing 22 and housing 24. A second hinge point can also be established using a hinge tab 78 attached to bearing cap 57 on casing 22 in a similar manner. Another way to establish the second hinge point is as shown in FIG. 4, in which an upstream hinge pin 80 is inserted into hinge tab 78 and through bearing cap 57. There is no hinge alignment bushing 60 at the second hinge point, as will be further explained below. It is to be appreciated, however, that alignment bushing 60 may be used at the upstream position (i.e. in cooperation with hinge pin 80) rather than at the downstream position as generally disclosed herein. The general function and cooperation of structure will be the same. With this in mind, and an understanding that though not shown in combination as an upstream alignment bushing, alignment bushing 60 will work as well in an upstream position.

Also provided are springs 66, 76 connected at attachment points 70, 74 of casing 22 and at attachment points 68, 72 of housing 24, respectively. Springs 66, 76 resist rotation of casing 22 about the hinge points of housing 24 as further explained below. It will be understood by a person of ordinary skill in the art, that the hinge mechanism as shown for the present invenion in FIG. 4 is only illustrative and that any arrangement whereby hinge action is estabished between casing 22 and housing 24 will suffice, provided it incorporates the functional characteristics to carry out the purpose of the invention as further described herein.

Figure 5:
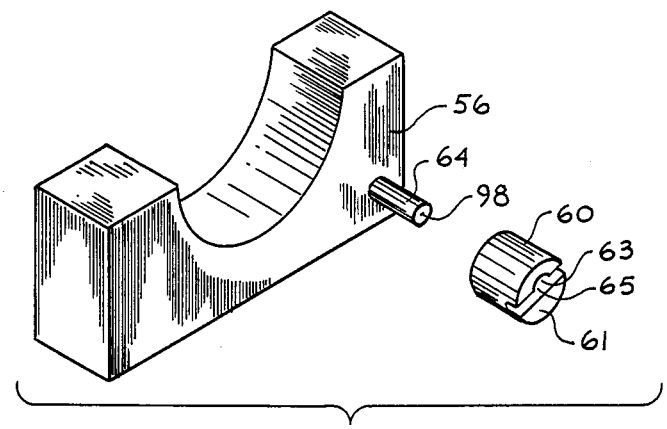
FIG. 5 is a perspective view of the aligning mechanism of the present invention.

With reference to FIG. 5, there is shown bearing cap 56 detached from casing 22 having hinge pin 64 extending therefrom. Hinge alignment bushing 60 is shown as being generally cylindrical-shaped and having a first face 61 through which there is a hole 63. Hole 63 extends through the bushing 60 and has an appropriate diameter for receiving the hinge pin 64.

In FIGS. 6A and 6B, alignment bushing 60 is shown mounted on hinge pin 64 of bearing cap 56. In FIG. 6A, the hinge alignment bushing 60 is shown in a reference position represented by zero degrees (0°). The bushing is capable of being rotated as indicated by arrow 89. In FIG. 6B, the alignment bushing 60 has been rotated one hundred eighty degrees (180°) in the direction of arrow 91 to the position shown. The hinge alignment bushing 60 may include a slot 65 adapted to accommodate an adjustment tool, such as a screw driver, for turning bushing 60 as will be further described below in the operation.

OPERATION

In operation of the pump 10, I.V. tube 16 is positioned between platen 28 and pumping mechanism 18. Camshaft 38 is mounted on casing 22 and drive motor 26 is operatively connected to camshaft 38 to cause its rotation. The consequent action of cams 44 on camshaft 38 causes linear reciprocal movement of the peristaltic fingers 30 within grooves 52 of housing 24. This movement causes a moving zone of occlusion against I.V. tube 16 for moving fluid therethrough.

The forces imparted by peristaltic fingers 30 against I.V. tube 16 are limited by the interaction of casing 22 with housing 24. Peristaltic fingers 30 are able to move into contact with I.V. tube 16 only to the point that any further force exerted against peristaltic fingers 30 will cause movement between casing 22 and housing 24. Thus, with reference to FIGS. 7A and 7B, any excessive back force created on peristaltic fingers 30 will be exerted through the fingers against camshaft 38 to rotate casing 22 in the direction of arrow 90 about hinge axis 98 relative to housing 24. Resistance to such rotational motion of casing 22 about hinge axis 98 is caused by action of springs 66 and 76 and their connections between casing 22 and housing 24.

Operation of the mechanism for maintaining linear flow of fluid through I.V. tube 16 can be further appreciated by across referencing FIG. 3, FIG. 6A, FIG. 6B, and FIGS. 7A and 7B. In particular, as shown in FIG. 3, at one point in the cycle, the first finger 30a is occluding the I.V. tube 16 at point 101. As suggested above, without some post-assembly adjustment, last finger 30b may occlude tube 16 at point 102 at the same time the first finger 30a is occluding tube 16 at point 101. This simultaneous occlusion may occur between cycles as a new cycle is just beginning at finger 30a and the last cycle is being completed at finger 30b. The result is the formation of an enclosed pocket 110 on tube 16 between the occlusion points 101 and 102. Also, as suggested above, any further urging by fingers 30 against pocket 110 increases fluid pressure in pocket 110 which will cause fluid to surge into the tube 16 when occlusion point 102 disappears.

To compensate for this, the present invention recognizes that the entire camshaft 38 may need to be tilted relative to platen 28, as shown in FIG. 3, from its original assembled orientation through an angle $\theta$. By tilting or raising the upstream or downstream end of camshaft 38, there is less unwanted pressure build up between points of occlusion 101 and 102 by first and last fingers 30a and 30b, respectively, thus reducing pressure and minimizing pulsatile flow. This then helps maintain linear flow. The amount of adjustment or tilting of camshaft 38 necessary is very minimal, typically only raising the camshaft 38 from one to five thousandths (0.001–0.005) of an inch at its upstream or downstream end.

As further illustrated in FIGS. 6A and 6B, it can be appreciated that rotation of the hinge alignment bushing 60 to a desired angle of rotation raises the bearing cap 56, and thus raises or lowers the entire camshaft 38 being carried on the bearing cap 56 by an amount 100. Since the hinge alignment bushing 60 is carried in the hole 62 of hinge tab 58, turning the hinge alignment bushing 60 one hundred eighty degrees (180°) as illustrated in FIG. 6B, causes the eccentric hole 63 carrying the hinge pin 64 to move the casing up the distance of 100, thereby tilting the camshaft 38 by that same amount. Any amount of adjustment may be maintained in between that shown in FIGS. 6A and 6B by turning the hinge alignment bushing 60 to an appropriated intermediate position.

This is further illustrated in FIGS. 7A and 7B. In FIG. 7A, the hinged axis of rotation 98 is shown in a first position corresponding to that of FIG. 6A represented by distance 103. In FIG. 7B, the hinge alignment bushing has been adjusted one hundred eighty degrees (180°), thereby raising the axis of rotation 98 so as to raise the downstream end of camshaft 38 to a distance 104.

In practice, such adjustments can take place while the peristaltic pump 10 is being operated to set the peristaltic pump mechanism at its optimal inclination of the camshaft 38 based on the tolerances experienced for that particular pump. Moreover, the optimal amount of adjustment could be further realized by making such adjustment while measuring the pressure within I.V. tube 16 with pressure sensor 50, and continually adjusting the hinge alignment bushing 60 to a setting where the fluid flow linearity is maximized and, consequently, the pulsatile nature of the flow is minimized. This provides for very fine tuning adjustment not heretofore experienced in any devices disclosed or taught in the prior art pumps.

It is to be understood that the relative motion between casing 22 and housing 24 about hinge axis 98 can be accomplished by various structures. In addition, it may be desirous to provide additional adjusting capability as may be required.

While the particular peristaltic pump as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. A linear peristaltic pump having a mechanism for maintaining linear flow of fluid through an I.V. tube comprising:
   a casing;
   a rotatable camshaft having an upstream end and a downstream end operatively mounted on said casing;
   a plurality of fingers coupled to said camshaft;
   a housing for establishing linear reciprocal movement of said fingers in response to rotation of said camshaft for establishing a moving zone of occlusion along said tube from an upstream end to a down stream end of said tube; and
   aligning means connecting said casing to said housing and adjustable to tilt said camshaft to prevent unwanted pressure build up in said tube and maintain substantially linear flow of fluid therethrough.

2. A linear peristaltic pump as recited in claim 1, further comprising means pivotally connecting said casing to said housing to establish an axis of rotation for said casing relative to said housing substantially parallel to the longitudinal axis of said camshaft.

3. A linear peristaltic pump as recited in claim 2 wherein said connecting means comprises a first hinge pin and a second hinge pin, and wherein said aligning means comprises an eccentric bushing mounted on said first hinge pin for moving said first hinge pin relative to said casing.

4. A linear peristaltic pump as recited in claim 3 wherein said bushing is adjustably mounted on said housing so that rotation of said bushing establishes an angle of tilt of said longitudinal axis of said camshaft to control its effect on the flow of fluid through said tube.

5. A linear peristaltic pump as recited in claim 4 further comprising a pressure sensing device for indicating fluid pressure in said tube.

6. A linear peristaltic pump as recited in claim 5 wherein said bushing includes a slot for allowing adjustable orientation of said bushing in said housing to minimize pulsatile flow in response to said indicated fluid pressure.

7. A linear peristaltic pump as recited in claim 5 wherein said bushing is located at the downstream end of said camshaft.

8. A linear peristaltic pump as recited in claim 6 wherein said bushing is located at the upstream end of said camshaft.

9. A method for adjusting a linear peristaltic pump of the type having a casing, a rotatable camshaft operatively mounted on the casing along an axis of rotation, a plurality of fingers coupled to the camshaft for establishing linear reciprocal movement of the fingers to provide a moving zone of occlusion against a tube, the tube having an upstream end and a downstream end, comprising the steps of:
   (a) rotating said camshaft;
   (b) observing the rate of change of pressure in said tube representing the rate of change of flow of fluid therethrough; and
   (c) tilting said rotating camshaft until said rate of fluid flow is observed to be substantially linear.

10. A linear peristaltic pump having a mechanism for establishing a substantially linear flow of fluid through an I.V. tube comprising:
    a casing carrying a rotatable camshaft having a plurality of cams spaced therealong;
    a plurality of fingers coupled to said cam;
    a housing hingedly connected to said casing for establishing linear reciprocal movement of said fingers in response to rotation of said camshaft to establish a moving zone of occlusion along said tube; and
    adjustable aligning means for establishing an axis of rotation of said camshaft which substantially linearizes the flow of fluid through said tube.

11. A linear peristaltic pump as recited in claim 10 wherein said casing includes a bearing cap having a hinge pin, and said housing includes a hinge tab, and wherein said aligning means comprises a cylindrical bushing rotatably mounted on said hinge tab and having an offset hole therethrough for receiving said hinge pin.

12. A linear peristaltic pump as recited in claim 11 wherein said bushing is rotatable to move said hinge pin relative to said housing.

13. A linear peristaltic pump as recited in claim 12 wherein said bushing is comprised of a plastic material.

14. A linear peristaltic pump as recited in claim 13 wherein said casing and said housing are biased together by means of a spring.

15. An adjustable linear peristaltic pump for pumping fluids through a resilient tube with substantially uniform flow which comprises:
    a camshaft;
    a plurality of linearly juxtaposed fingers including a first finger and a last finger, each of said fingers being operatively engaged with said camshaft;
    a platen for holding said tube against said fingers;
    means for rotating said camshaft to sequentially and cyclically urge said fingers against said tube to create a moving zone of occlusion therealong; and
    means for tilting said camshaft relative to said platen to open the occlusion at said last finger as said first finger occludes said tube.

16. An adjustable linear peristaltic pump as recited in claim 15 wherein said means for tilting said camshaft includes a bushing associated with said camshaft having eccentric means for pivotally coupling said camshaft to said platen.

17. An adjustable linear peristaltic pump as recited in claim 16 wherein said eccentric means comprises said bushing having an offset hole for receiving a hinge pin.

* * * * *